(12) United States Patent
Ward

(10) Patent No.: US 7,722,677 B2
(45) Date of Patent: *May 25, 2010

(54) URETERAL STENT WITH CONFORMING RETENTION STRUCTURE

(75) Inventor: Tim Ward, Springville, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/145,238

(22) Filed: Jun. 24, 2008

(65) Prior Publication Data

US 2008/0255679 A1    Oct. 16, 2008

Related U.S. Application Data

(63) Continuation of application No. 11/126,289, filed on May 11, 2005, now Pat. No. 7,396,366.

(51) Int. Cl.
    *A61F 2/04* (2006.01)
(52) U.S. Cl. .......................................... 623/23.66; 604/8
(58) Field of Classification Search ..... 623/23.66–23.7; 604/8
    See application file for complete search history.

(56) References Cited

U.S. PATENT DOCUMENTS

| 3,108,593 A | 10/1963 | Glassman |
| 3,890,977 A | 6/1975 | Wilson |
| 4,134,402 A | 1/1979 | Mahurkar |
| 4,202,332 A | 5/1980 | Tersteegen et al. |
| 4,212,304 A | 7/1980 | Finney |
| 4,307,723 A | 12/1981 | Finney |
| 4,334,327 A | 6/1982 | Lyman et al. |
| 4,403,983 A | 9/1983 | Edelman et al. |
| 4,416,267 A | 11/1983 | Garren et al. |
| 4,531,933 A | 7/1985 | Norton et al. |
| 4,568,338 A | 2/1986 | Todd |
| 4,580,568 A | 4/1986 | Gianturco |

(Continued)

FOREIGN PATENT DOCUMENTS

DE    42 13 480 A    10/1993

(Continued)

OTHER PUBLICATIONS

"Specific gravity of major polymers", 1999, http:--www.plasticusa.com-specgrav.html.
Hepperlen, T., et al., Self-Retained Internal Ureteral Stents: A New Approach, The Journal of Urology, vol. 119 (1978), pp. 731-734.

(Continued)

*Primary Examiner*—Suzette J Gherbi

(57) ABSTRACT

A ureteral stent includes an elongate member defining an axis and having a proximal end portion and a distal end portion. A first extension member and a second extension member extend from the proximal end portion and each include a first portion, a second portion, a third portion and an end portion. In an unconstrained configuration, the first portion is arcuate and extends away from the axis, the second portion extends from the first portion in a distal direction, and the third portion extends from the second portion in a direction away from the axis. In the unconstrained configuration, the end portions of the first and second extension members are spaced apart from each other sufficiently, and the first extension member and the second extension member are sufficiently rigid, to collectively help retain at least a portion of the ureteral stent within a bladder of a patient.

21 Claims, 11 Drawing Sheets

U.S. PATENT DOCUMENTS

| | | |
|---|---|---|
| 4,583,968 A | 4/1986 | Mahurkar |
| 4,610,657 A | 9/1986 | Densow |
| 4,643,716 A | 2/1987 | Drach |
| 4,671,795 A | 6/1987 | Mulchin |
| 4,713,049 A | 12/1987 | Carter |
| 4,738,667 A | 4/1988 | Galloway |
| 4,762,128 A | 8/1988 | Rosenbluth |
| 4,782,834 A | 11/1988 | Maguire et al. |
| 4,787,884 A | 11/1988 | Goldberg |
| 4,790,810 A | 12/1988 | Pugh, Jr. et al. |
| 4,813,925 A | 3/1989 | Anderson, Jr. et al. |
| 4,820,262 A | 4/1989 | Finney |
| 4,846,814 A | 7/1989 | Ruiz |
| 4,874,360 A | 10/1989 | Goldberg et al. |
| 4,887,996 A | 12/1989 | Bengmark |
| 4,931,037 A | 6/1990 | Wetterman |
| 4,950,228 A | 8/1990 | Knapp, Jr. et al. |
| 4,973,301 A | 11/1990 | Nissenkorn |
| 4,990,133 A | 2/1991 | Solazzo |
| 5,019,102 A | 5/1991 | Hoene |
| 5,052,998 A | 10/1991 | Zimmon |
| 5,057,073 A | 10/1991 | Martin |
| 5,078,736 A | 1/1992 | Behl |
| 5,112,310 A | 5/1992 | Grobe |
| 5,116,309 A | 5/1992 | Coll |
| 5,141,502 A | 8/1992 | Macaluso, Jr. |
| 5,176,625 A | 1/1993 | Brisson |
| 5,176,626 A | 1/1993 | Soehendra |
| 5,221,253 A | 6/1993 | Coll |
| 5,224,953 A | 7/1993 | Morgentaler |
| 5,234,456 A | 8/1993 | Silvestrini |
| 5,269,802 A | 12/1993 | Garber |
| 5,282,784 A | 2/1994 | Willard |
| 5,322,501 A | 6/1994 | Mahmud-Durrani |
| 5,346,467 A | 9/1994 | Coll |
| 5,354,263 A | 10/1994 | Coll |
| 5,364,340 A | 11/1994 | Coll |
| 5,380,270 A | 1/1995 | Ahmadzadeh |
| 5,401,257 A | 3/1995 | Chevalier, Jr. et al. |
| 5,507,769 A | 4/1996 | Marin et al. |
| 5,514,088 A | 5/1996 | Zakko |
| 5,514,176 A | 5/1996 | Bosley, Jr. |
| 5,518,498 A | 5/1996 | Lindenberg et al. |
| 5,520,697 A | 5/1996 | Lindenberg et al. |
| 5,531,741 A | 7/1996 | Barbacci |
| 5,599,291 A | 2/1997 | Balbierz et al. |
| 5,647,843 A | 7/1997 | Mesrobian et al. |
| 5,662,713 A | 9/1997 | Andersen et al. |
| 5,681,274 A | 10/1997 | Perkins et al. |
| 5,683,448 A | 11/1997 | Cragg |
| 5,709,874 A | 1/1998 | Hanson et al. |
| 5,716,393 A | 2/1998 | Lindenberg et al. |
| 5,755,722 A | 5/1998 | Barry et al. |
| 5,766,209 A | 6/1998 | Devonec |
| RE35,849 E | 7/1998 | Soehendra et al. |
| 5,795,319 A | 8/1998 | Ali |
| 5,827,276 A | 10/1998 | Le Veen et al. |
| RE35,988 E | 12/1998 | Winston et al. |
| 5,885,258 A | 3/1999 | Sachdeva et al. |
| 5,891,111 A | 4/1999 | Ismael |
| 5,907,893 A | 6/1999 | Zadno-Azizi et al. |
| 5,913,852 A | 6/1999 | Magram |
| 5,928,280 A | 7/1999 | Hansen et al. |
| 5,957,912 A | 9/1999 | Heitzmann |
| 5,964,744 A | 10/1999 | Balbierz et al. |
| 5,968,088 A | 10/1999 | Hansen et al. |
| 5,971,967 A | 10/1999 | Willard |
| 6,007,558 A | 12/1999 | Ravenscroft et al. |
| 6,013,854 A | 1/2000 | Moriuchi |
| 6,086,553 A | 7/2000 | Akbik |
| 6,102,888 A | 8/2000 | Walker |
| 6,110,212 A | 8/2000 | Gregory |
| 6,176,875 B1 | 1/2001 | Lenker et al. |
| 6,206,849 B1 | 3/2001 | Martin et al. |
| 6,258,098 B1 * | 7/2001 | Taylor et al. ................ 606/108 |
| 6,332,892 B1 | 12/2001 | Desmond, III et al. |
| 6,364,868 B1 | 4/2002 | Ikeguchi |
| 6,569,150 B2 | 5/2003 | Teague et al. |
| 6,626,858 B2 | 9/2003 | Lynch et al. |
| 6,648,863 B2 | 11/2003 | Reever |
| 6,767,339 B2 | 7/2004 | Reydel |
| 6,849,069 B1 | 2/2005 | Clayman et al. |
| 6,908,447 B2 | 6/2005 | McWeeney et al. |
| 6,926,690 B2 | 8/2005 | Renati |
| 6,929,621 B2 | 8/2005 | Whitmore et al. |
| 7,396,366 B2 * | 7/2008 | Ward ........................ 623/23.66 |
| 2001/0047164 A1 | 11/2001 | Teague et al. |
| 2001/0049494 A1 | 12/2001 | Liu |
| 2001/0053936 A1 | 12/2001 | Whitmore |
| 2002/0007222 A1 | 1/2002 | Desai |
| 2002/0032487 A1 | 3/2002 | Dua et al. |
| 2002/0033180 A1 | 3/2002 | Solem |
| 2002/0173754 A1 | 11/2002 | Whitmore, III |
| 2002/0183852 A1 | 12/2002 | McWeeney |
| 2003/0109930 A1 | 6/2003 | Bluni et al. |
| 2003/0199805 A1 | 10/2003 | McWeeney |
| 2004/0193092 A1 | 9/2004 | Deal |
| 2005/0131547 A1 | 6/2005 | Segura et al. |
| 2005/0240141 A1 | 10/2005 | Aliski et al. |
| 2005/0240279 A1 | 10/2005 | Kagan et al. |
| 2008/0249636 A1 * | 10/2008 | Deal ........................ 623/23.66 |

FOREIGN PATENT DOCUMENTS

| | | |
|---|---|---|
| EP | 1 062 920 A1 | 12/2000 |
| WO | WO 96/11721 A | 4/1996 |
| WO | WO 97/17094 A | 5/1997 |
| WO | WO 99/24106 A1 | 5/1999 |
| WO | WO 99/58083 A1 | 11/1999 |
| WO | WO 00/51521 A1 | 9/2000 |
| WO | WO 00/66032 A1 | 11/2000 |
| WO | WO 00/74582 | 12/2000 |
| WO | WO 01/91668 A1 | 12/2001 |
| WO | WO 03/049796 A1 | 6/2003 |

OTHER PUBLICATIONS

Camacho, M.F., et al., Double-Ended Pigtail Ureteral Stent: Useful Modification to Single End Ureteral Stent, Urology, vol. 13, No. 5 (May 1979), pp. 516-520.

Mardis, H. K., et al., Double Pigtail Ureteral Stent, Urology, vol. 14, No. 1, (Jul. 1979), pp. 23-26.

Mardis, H. K., et al., Polyethylene Double-Pigtail Ureteral Stents, Urologic Clinics of North America, vol. 9, No. 1 (Feb. 1982), pp. 95-101.

Stables, D. Percutaneous Nephrostomy: Techniques, Indications, and Results, Urologic Clinics of North America, vol. 9, No. 1 (Feb. 1982), pp. 15-29.

Minkov, N., et al., Our Experience in the Application of the Biocompatible Indwelling Ureteral Stents, International Urology and Nephrology, vol. 18, No. 4 (1986), pp. 403-409.

Mardis, H. K., Evaluation of Polymeric Materials for Endourologic Devices, Seminars in Interventional Radiology, vol. 4, No. 1, (Mar. 1987), pp. 36-45.

Birch, B.R.P., et al., Tethered Ureteric-Stents—A Clinical Assessment, British Journal of Urology, vol. 62, (1988), pp. 409-411.

Mardis, H. K., et al., Ureteral Stents, Urologic Clinics of North America, vol. 15, No. 3 (1988), pp. 471-479.

Bard Urological Division—Product Catalog (1990).

Cook Urological—Urological Surgical Products (1990), pp. 176-228.

Mardis, H. K., et al., Ureteral Stents: Use and Complications, Problems in Urology, vol. 6, No. 2 (Jun. 1992), pp. 296-306.

Mardis, H. K., et al., Comparative Evaluation of Materials Used for Internal Ureteral Stent, Journal of Endourology, vol. 7, No. 2 (1993), pp. 105-115.

Culkin, D. J., Complications of Ureteral Stents, Infections in Urology (Sep. 1996), pp. 139-143.

Mardis, H. K., et al., Self-Retained Internal Ureteral Stents: Use and Complications, AUA Update Series, Lesson 29, vol. 16 (1997), pp. 226-232.

International Search Report dated Jul. 26, 2006, for International Application No. PCT-US2006-009283, 4 pages.

* cited by examiner

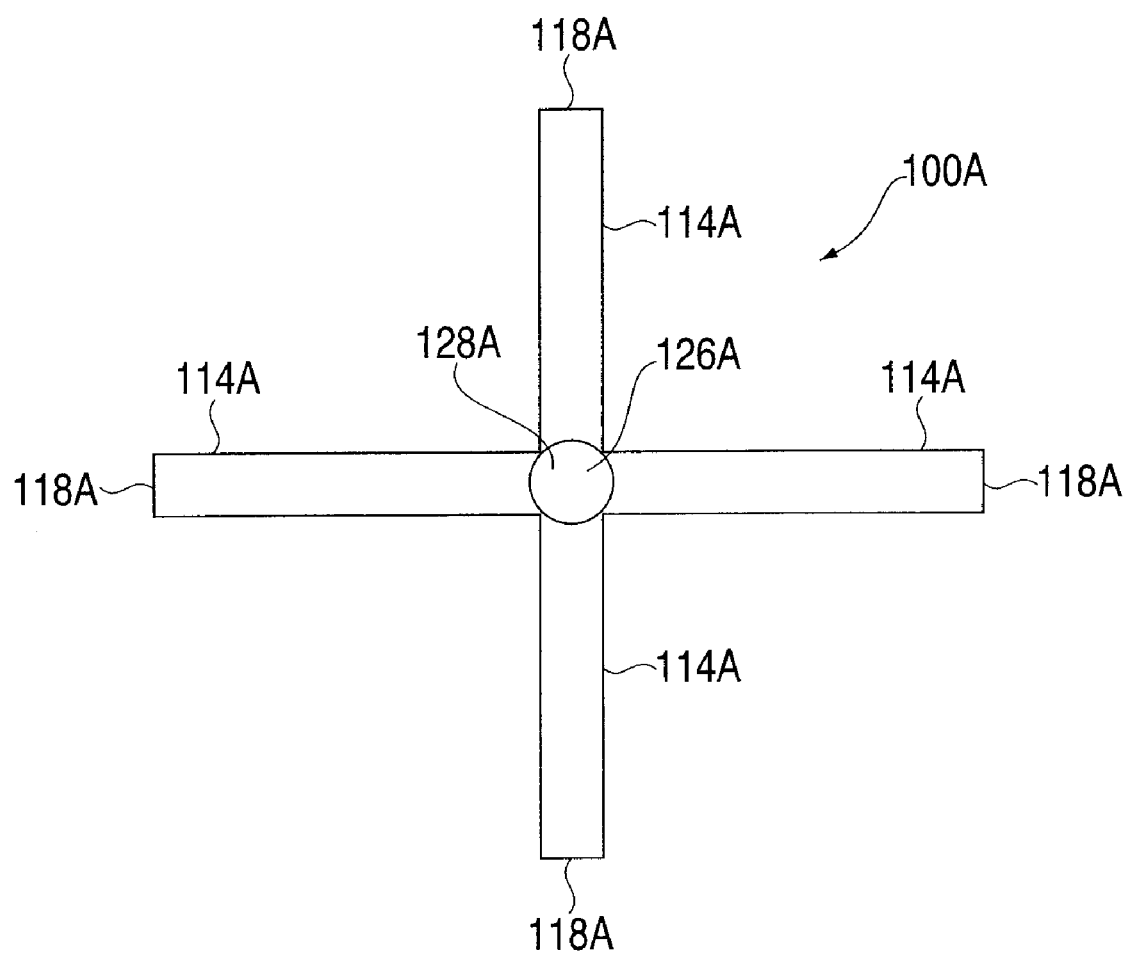

US 7,722,677 B2

URETERAL STENT WITH CONFORMING RETENTION STRUCTURE

CROSS-REFERENCE TO RELATED APPLICATIONS

This application claims priority to and is a continuation of U.S. patent application Ser. No. 11/126,289, filed May 11, 2005, now U.S. Pat. No. 7,396,366 and entitled "Ureteral Stent With Conforming Retention Structure," the disclosure of which is incorporated herein by reference in its entirety.

BACKGROUND

The disclosed invention relates generally to a medical device and more particularly to a ureteral stent having a conforming retention structure to provide improved patient comfort.

Known ureteral stents are typically placed within a urinary tract of a patient such that one end portion of the ureteral stent is located in either a kidney or a ureter of the patient and another end portion of the ureteral stent is located in a bladder of the patient. Some known ureteral stents include retention members configured to help retain the ureteral stent in position within the patient. Known ureteral stents are typically positioned within the urinary tract of the patient by placing a guidewire within the patient, sliding the ureteral stent on the guidewire, and then forcing the ureteral stent along the guidewire into a desired position within the patient using a push cannula. Such ureteral stents are often removed from the patient by pulling the ureteral stent from the urinary tract of the patient.

Known ureteral stents often cause discomfort to the patient once the ureteral stents are positioned within the body due to the size and mass of the retention members. For example, some ureteral stents include a curled end portion that may be positioned in a bladder of a patient to help retain the ureteral stent in place within the patient. The large mass of the curled retention structure does not easily conform to the bladder when the bladder is emptied or collapsed, resulting in patient discomfort. Further discomfort can also result when the ureteral stent is removed from a patient due to the configuration of the retention member.

Thus, there is a need for a ureteral stent having a retention portion that distributes the mass of the retention structure within the bladder and conforms to the shape of the bladder walls to help reduce pain and discomfort to the patient.

SUMMARY OF THE INVENTION

A ureteral stent includes an elongate member defining an axis and having a proximal end portion and a distal end portion. A first extension member and a second extension member extend from the proximal end portion of the elongate member. The first extension member and the second extension member each include a first portion, a second portion, a third portion and an end portion. In an unconstrained configuration, the first portion is arcuate and extends away from the axis defined by the elongate member, the second portion extends from the first portion in a distal direction, and the third portion extends from the second portion in a direction away from the axis defined by the elongate member. In the unconstrained configuration, the end portion of the first extension member and the end portion of the second extension member are spaced apart from each other sufficiently, and the first extension member and the second extension member are sufficiently rigid, to collectively help retain at least a portion of the ureteral stent within a bladder of a patient.

BRIEF DESCRIPTION OF THE DRAWINGS

The present invention is described with reference to the accompanying drawings. In the drawings, like reference numbers indicate identical or functionally similar elements. For example item 100 is identical or functionally similar to item 100A.

FIG. 2B is a bottom view of the ureteral stent shown in FIG. 2A.

DETAILED DESCRIPTION

Figure 1:
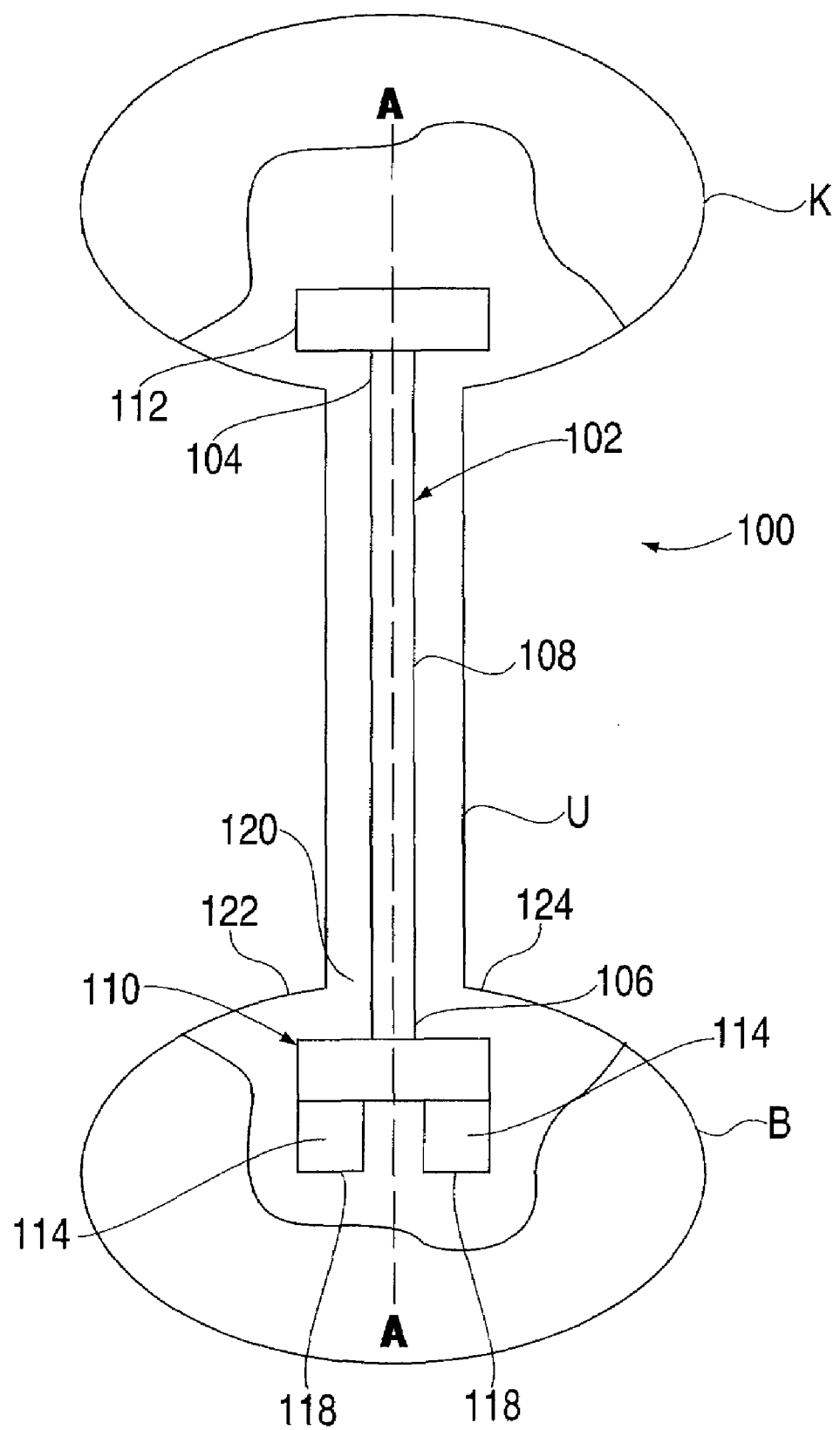
FIG. 1 is a schematic illustration of a ureteral stent according to an embodiment of the invention.

FIG. 1 is a schematic illustration of a ureteral stent 100 disposed within a urinary tract of a patient. Specifically, the ureteral stent 100 is placed or otherwise implanted into the urinary tract of a patient such that the ureteral stent 100 extends through the ureter U, from the kidney K of the patient to the bladder B of the patient. The ureteral stent 100 is configured to help facilitate the movement of fluid within a urinary tract of a patient.

The ureteral stent 100 includes an elongate member 102 having a distal end portion 104, a proximal end portion 106, and a medial portion 108. A retention portion 110 extends from the proximal end portion 106 of the elongate member 102. Similarly, a retention portion 112 extends from the distal end portion 104 of the elongate member 102. The elongate member 102 defines an axis A and a lumen (not shown in FIG. 1). The lumen may extend from the distal end portion 104 to the proximal end portion 106 of the elongate member 102. The elongate member 102 further defines an opening (not shown in FIG. 1) on the proximal end portion of the elongate member 102 that communicates with the lumen. In other embodiments, the lumen may not extend from the distal end portion 104 to the proximal end portion 106. Rather, the lumen may only extend through a portion of the elongate member 102. In yet another embodiment, the elongate member 102 does not include an opening on the proximal end portion that communicates with the lumen.

The retention portion 112 extends from the distal end portion 104 of the elongate member 102 and is configured to be placed in the kidney K of the patient. The retention portion 112 is configured to help prevent migration of the ureteral stent 100 downwardly toward the bladder B. Accordingly, the retention member 112 is configured to help retain at least a portion of the ureteral stent 100 within the kidney K of the patient. Retention portion 112 may be configured in a variety of different shapes and sizes. For example, the retention portion 112 may include a coil portion or a loop portion.

The retention portion 110 extends from the proximal end portion 106 of the elongate member 102 and is configured to be placed within the bladder B of the patient. The retention portion 106 is configured to help prevent migration of the ureteral stent 100 upwardly toward the kidney K of the patient. Accordingly, the retention portion 110 is configured to help retain at least a portion of the ureteral stent 100 within the bladder B of the patient. Retention portion 110 includes one or more extension members 114 that extend from the proximal end portion 106 of the elongate member 102. In the embodiment shown in FIG. 1, retention portion 110 includes two extension members 114. Each extension member 114 includes an end portion 118. Each of the extension members 114 may be formed monolithically with the elongate member 102. Alternatively, the extension members 114 may be coupled to the elongate member 102 such as, for example, via an adhesive or a mechanical coupling. Although two extension members are illustrated in FIG. 1, it should be understood that any number of extension members can be used as will be shown in other embodiments.

Extension members 114 may be configured in a variety of different shapes and sizes, and are flexible yet sufficiently rigid to collectively help retain at least a portion of the ureteral stent 100 within the bladder B of the patient. The extension members 114 are configurable between an unconstrained configuration and a constrained configuration. In the unconstrained configuration, the end portions 118 of the extension members 114 are spaced apart from each other such that the distance between at least two extension members 114 is greater than a ureter entrance 120. Specifically, one of the extension members 114 is configured to contact a bladder wall of the patient at a first contact location 122 and the other extension member 114 is configured to contact the bladder wall of the patient at a second contact location 124. The first contact location 122 and the second contact location 124 are disposed at a spaced distance from the ureter entrance 120 of the patient. The extension members 114 are configurable to the constrained configuration by urging the end portions 118 of the extension members 114 such that the extension members 114 are positioned substantially adjacent each other, which will be discussed in more detail below.

Although the ureteral stent 100 is illustrated and described as being configured to extend from the kidney K of the patient to the bladder B of the patient, it is not necessary that ureteral stent 100 be configured to extend from the kidney K to the bladder B. For example, in another embodiment, the ureteral stent is configured to extend from the ureter U of the patient to a location within the bladder B of the patient.

In one embodiment, ureteral stent 100 is implanted into the urinary tract of the patient by inserting the stent 100 into the patient transuretherally. For example, a guidewire may be placed within the urinary tract of the patient. Subsequently, the ureteral stent 100 may be placed on the guidewire and forced into a desired position within the urinary tract of the patient such as via a pusher device. In another embodiment, ureteral stent 100 is implanted into the urinary tract of the patient by inserting the stent 100 into the patient transdermally or percutaneously.

The ureteral stent 100 may be formed from a number of different biocompatible materials. The ureteral stent 100 may consist of one material or may be formed, for example by extrusion, of two or more materials along its length. For example, in one embodiment, the distal end portion 104 of the ureteral stent 100 is formed from a first material having a first durometer and the proximal end portion 106 is formed from a second material, which is softer and/or more flexible than the first material, having a second durometer different than the first durometer. Accordingly, the proximal end portion 106 may be made of a softer or more flexible material than that of the distal end portion 104, and vice versa.

The ureteral stent 100 may be formed from any material or materials known in the art to be used in constructing ureteral stents. One subset of biocompatible materials best suited for the ureteral stent 100 exhibit at least some of the following characteristics: high tensile strength, high retention coil strength, excellent biocompatibility and biodurability, excellent radiopacity or fluoroscopic visibility, availability in varying durometers, and a low resistance to passage. For example, in one embodiment, the ureteral stent 100 is formed from a polymeric material.

Figure 2A:
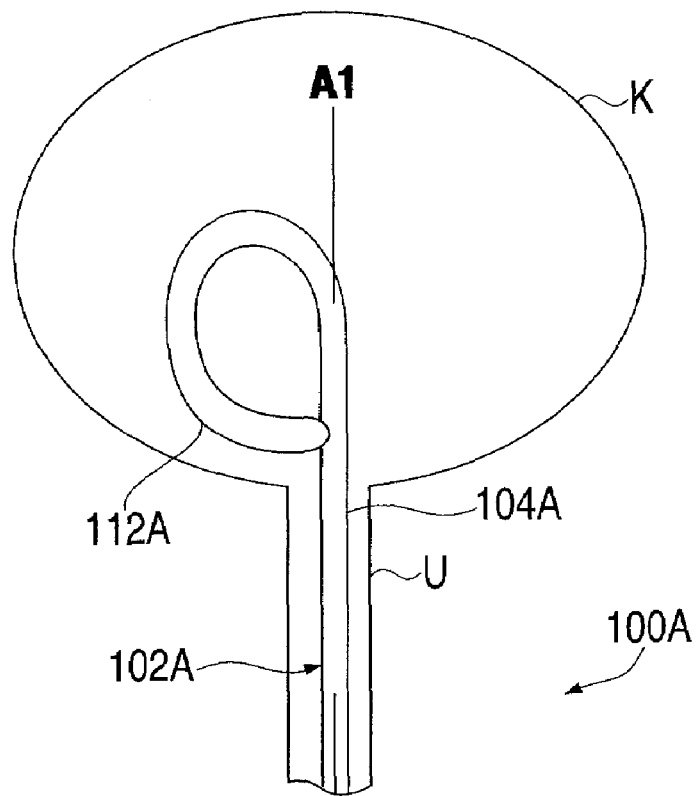
FIG. 2A is side view of a ureteral stent according to an embodiment of the invention shown positioned in a kidney, ureter and bladder of a patient.
Figure 2A:
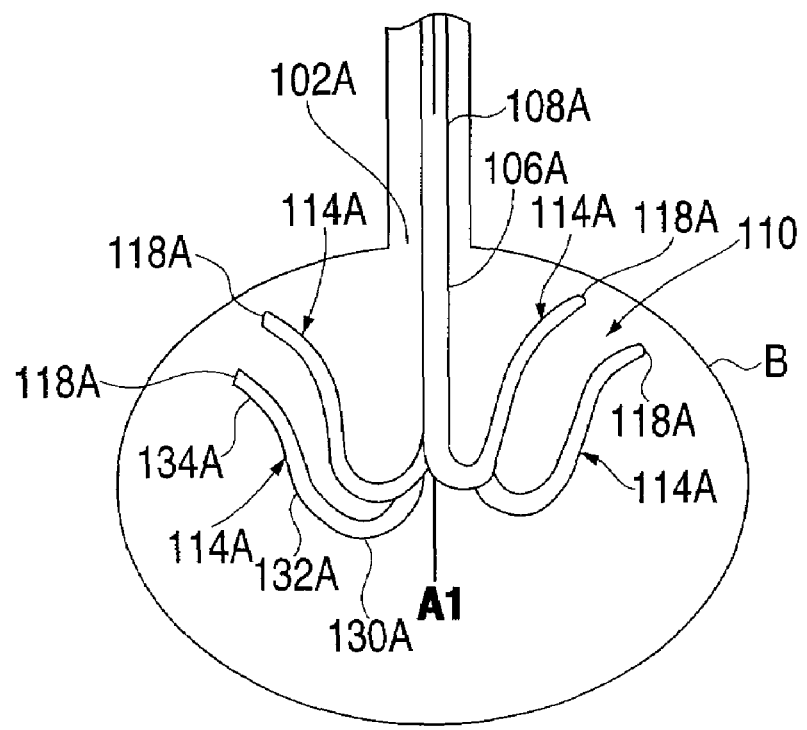

FIG. 2A illustrates a ureteral stent according to one embodiment of the invention. The ureteral stent 100A is configured to be implanted into a urinary tract of a patient such that the ureteral stent 100A extends from a kidney K of the patient to a bladder B of the patient. In this embodiment, the ureteral stent 100A includes an elongate member 102A having a distal end portion 104A, a proximal end portion 106A, and a medial portion 108A. The elongate member 102A defines an axis A1. A retention member 112A extends from the distal end portion 104A of the elongate member 102A and is configured to be placed and retained in the kidney K of the patient. A retention portion 110A extends from the proximal end portion 106A of the elongate member 102A and is configured to be placed and retained in the bladder B of the patient. The elongate member 102A defines a lumen 126A and an opening 128A in communication with the lumen 126A, as shown in FIG. 2B.

Retention portion 110A includes four extension members 114A extending from the proximal end portion 106A of the elongate member 102A. The extension members 114A each have an end portion 118A, as shown in FIGS. 2A and 2B. Extension members 114A may be formed monolithically with elongate member 102A. For example, extension members 114A may be formed by slitting plastic tubing used to construct elongate member 102A with a cutting device. For example, the plastic tubing may be split as described in United States Patent Application Publication No. US-2004-0193092-A1, which is hereby incorporated by reference in its entirety. The extension members 114A are then formed into a selected shape. Splitting the elongate member 102A to form the extension members 114A spreads the mass of the retention member 102A into different regions within the bladder of the patient. The separate extension members 114A conform to the shape of the bladder of the patient, thereby providing more patient comfort. In addition, the extension members 114A extend in a direction away from the axis A1 and the opening 128A defined by the elongate member 102A. Thus, because the extension members 114A extend away from the axis A1 and the opening 128A, a guidewire may be easily inserted into the lumen 126A via the opening 128A.

Specifically, the extension members 114A each include a first arcuate portion 130A extending away from the axis A1 defined by the elongate member 102A, a second portion 132A extending in a distal direction and a third portion extending from the second portion 132A in a direction away from the axis A1 defined by the elongate member 102A. In some embodiments, the first arcuate portion 130A extends from the proximal end portion of the elongate member and curves in a first direction approximately 180 degrees (see e.g., FIGS. 2A, 3A, 3B, 3C, 3D and 4).

Figure 3A:
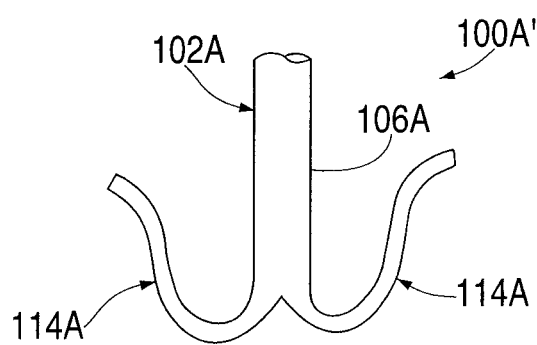
FIG. 3A is a side view of a portion of a ureteral stent according to an embodiment of the invention.
Figure 3B:
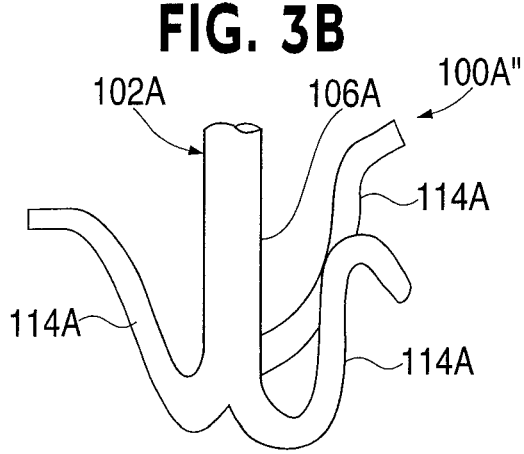
FIG. 3B is a side view of a portion of a ureteral stent according to an embodiment of the invention.
Figure 3C:
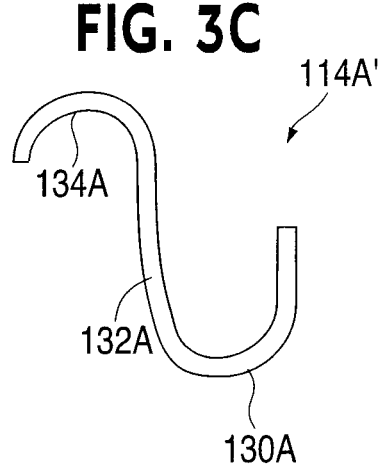
FIGS. 3C-3F are side views of extension members according to several embodiments of the invention.
Figure 3D:
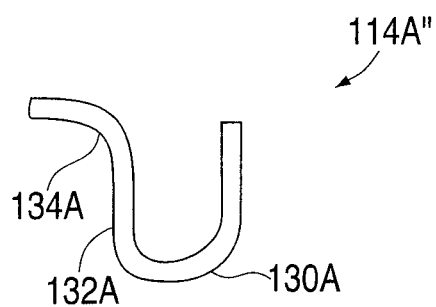
Figure 3E:
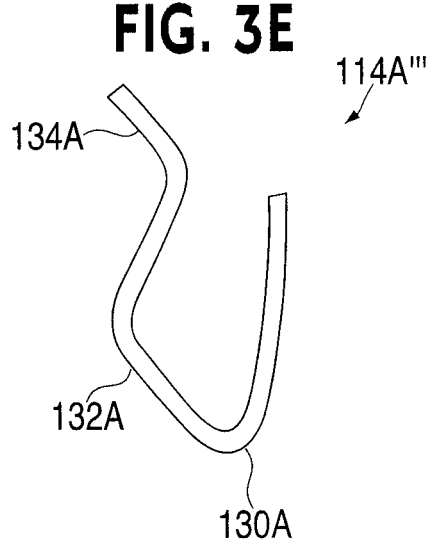
Figure 3F:
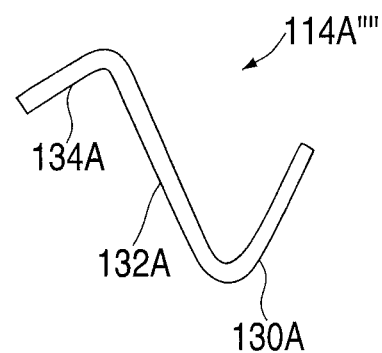

The ureteral stent may include any number of extension members 114A. For example, a ureteral stent 100A' includes two extension members 114A extending from the proximal end portion 106A of the elongate member 102A, as shown in FIG. 3A. In another example, a ureteral stent 100A" includes three extension members 114A extending from the proximal end portion 106A of the elongate member 102A, as shown in FIG. 3B. In addition, the extension members 114A may be configured in a variety of different shapes and sizes, while still including a first arcuate portion 130A, a second portion 132A and a third portion 134A as described above. Other embodiments of extension members are shown in FIGS. 3C through 3F. Specifically, extension members 114'-114"" are shown in FIGS. 3C through 3F, respectively.

Figure 4:
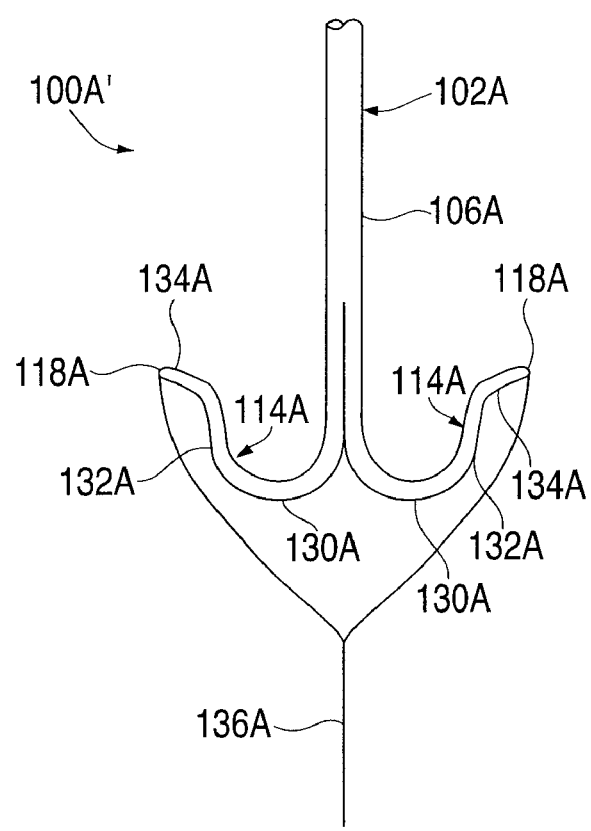
FIG. 4 is a side view of a portion of the ureteral stent of FIG. 3A shown in an unconstrained configuration.
Figure 5A:
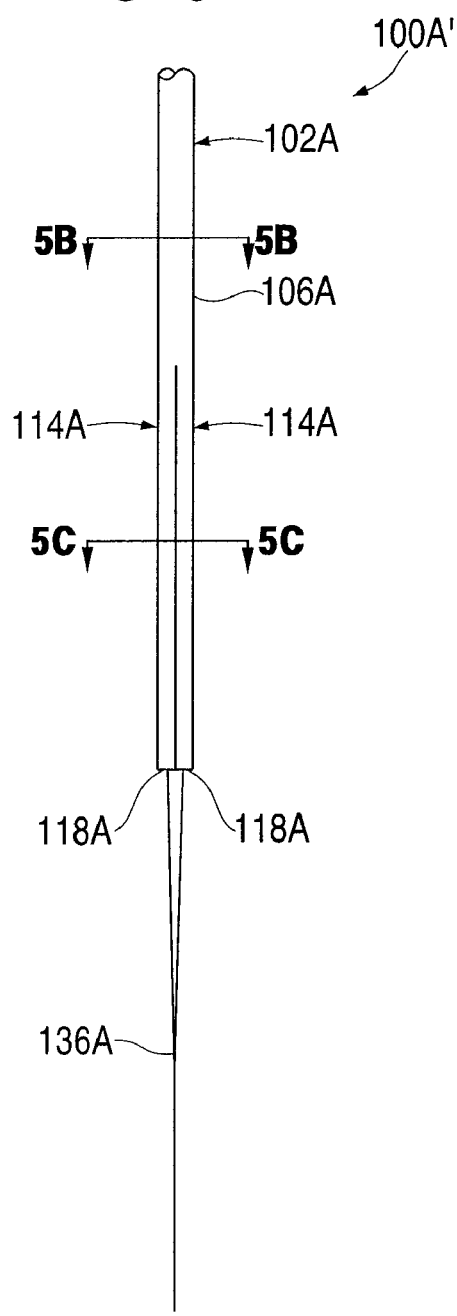
FIG. 5A is a side view of the portion of the ureteral stent of FIGS. 3A and 4 shown in a constrained configuration.
Figure 5B:
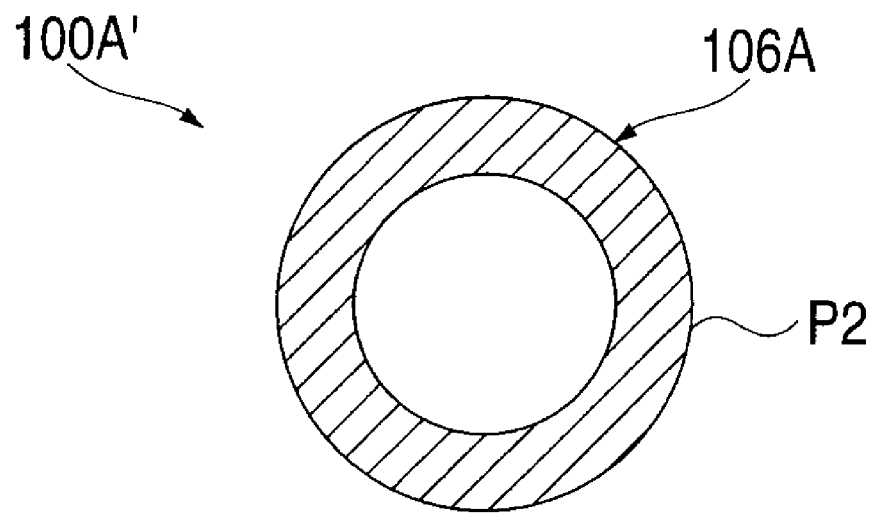
FIG. 5B is a cross-sectional view taken along line 5B-5B in FIG. 5A.
Figure 5C:
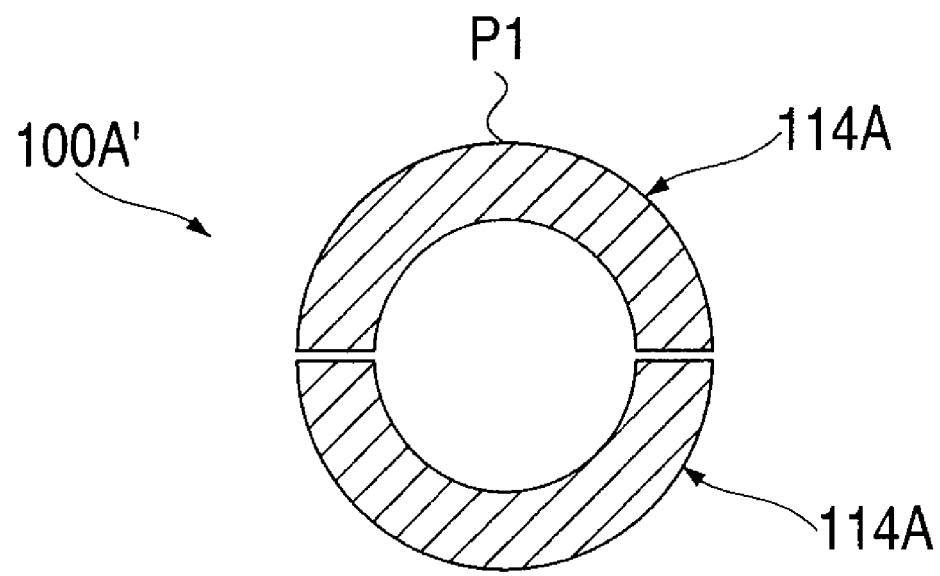
FIG. 5C is a cross-sectional view taken along line 5C-5C in FIG. 5A

FIG. 4 illustrates a portion of stent 100A' shown in an unconstrained configuration. The extension members 114A are each configured to contact a bladder wall of the patient at a contact location that is spaced at a distance from a ureter entrance 120A of the patient. As shown in FIG. 4, a tether 136A may be coupled to end portions 118A of the extension members 114A. To withdraw the ureteral stent 100A' from the ureter of a patient, the tether 136A is pulled proximally, which urges the end portions 118A proximally and into a constrained configuration, as shown in FIG. 5A. The extension members 114A may be urged to the constrained configuration sequentially or simultaneously. In addition, the ureteral stent 100A' may be withdrawn from the ureter of a patient by urging the ureteral stent 100A' along a guidewire. In the constrained configuration, the extension members 114A are positioned substantially adjacent each other. In other words, when the ureteral stent 100A' is in its constrained configuration there is no more than a substantially small gap between the extension members 114A. For example, in one embodiment, when the ureteral stent is in its constrained configuration, the extension members are disposed 0.1 mm away from each other. In another embodiment, when the ureteral stent is in its constrained configuration, the extension member are abutting each other. In addition, in the constrained configuration, the extension members 114A collectively define a perimeter P1, as shown in FIG. 5C, and the elongate member 102A defines a perimeter P2, as shown in FIG. 5B. The perimeter P2 defined by the elongate member 102A is substantially the same size as the perimeter P1 defined collectively by the extension members 114A. In some embodiments, in the constrained configuration the extension members 114A are capable of being contained within the perimeter P2 of the elongate member 102A.

Figure 6:
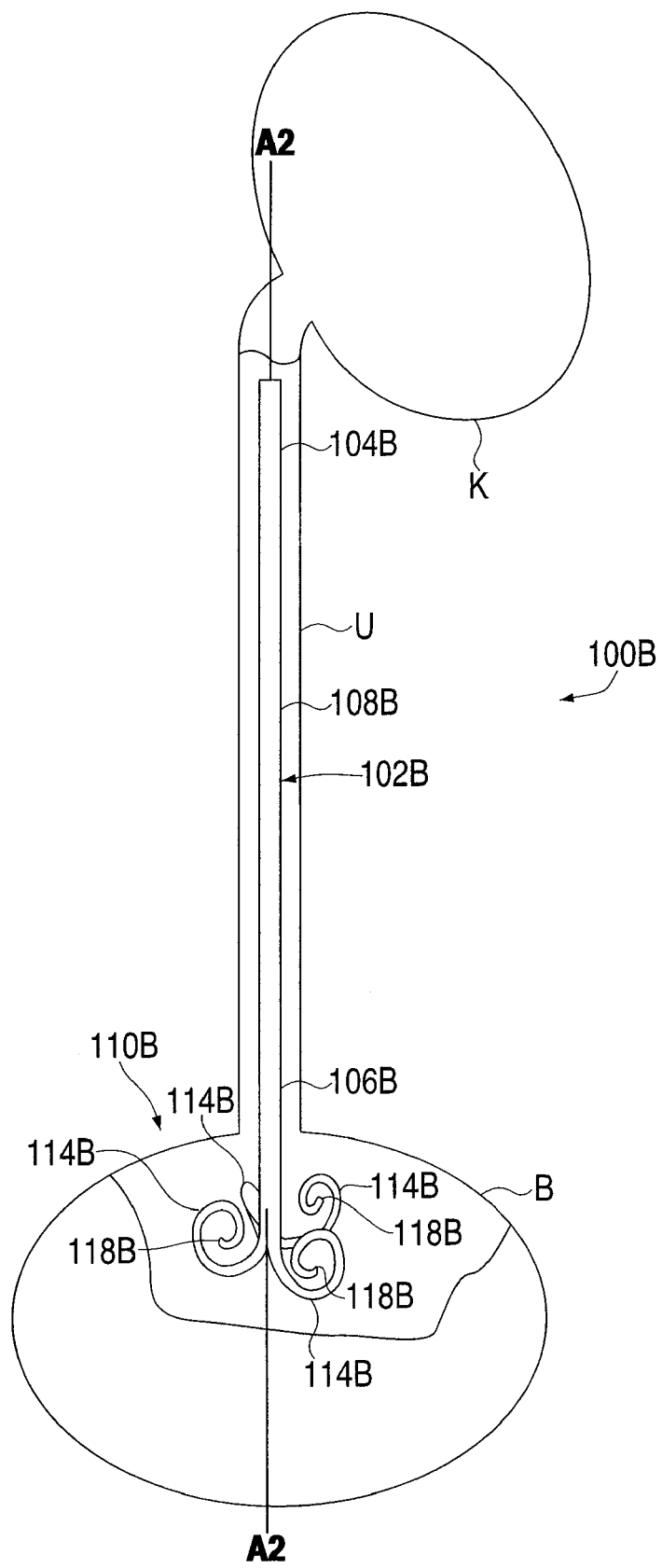
FIG. 6 is a side view of a ureteral stent according to another embodiment of the invention shown positioned in a ureter and bladder of a patient.

FIG. 6 illustrates a ureteral stent according to another embodiment of the invention. Ureteral stent 100B includes an elongate member 102B having a distal end portion 104B, a medial portion 108B and a proximal end portion 106B. In this embodiment, the distal end portion 104B does not include a retention portion. The distal end portion 104B of the elongate member 102B is configured to be positioned within a ureter U of a patient. A retention portion 110B, similar to the retention portion 110A, extends from the proximal end portion 106B of the elongate member 102B. The retention portion 110B includes four extension members 114B, which are constructed substantially the same as the previous embodiments and perform substantially the same functions as the previous embodiments. The extension members 114B each extend from the proximal end portion 106B of the elongate member 102B in a direction away from an axis A2 defined by the elongate member 102B. The extension members 114B each include an end portion 118B.

The extension members 114B have the same properties when positioned in an unconstrained configuration and a constrained configuration as with the previous embodiments. For example, the end portions 118B of the extension members 114B are disposed apart from each other and contact the bladder wall at a spaced distance from a ureter opening when the ureteral stent 100B is in its unconstrained configuration. In addition, the extension members 114B may be urged into a constrained configuration in the same manner as previously described. In the constrained configuration, a perimeter defined collectively by the extension members 114B is substantially the same size as a perimeter defined by the elongate member 102B.

The extension members 114B differ from extension members 114A in that they each include a coil configuration extending in a direction away from the axis A2 defined by the elongate member 102B. The coil configuration of each of the extension members 114B includes at least one complete turn as shown in FIG. 6.

Figure 7A:
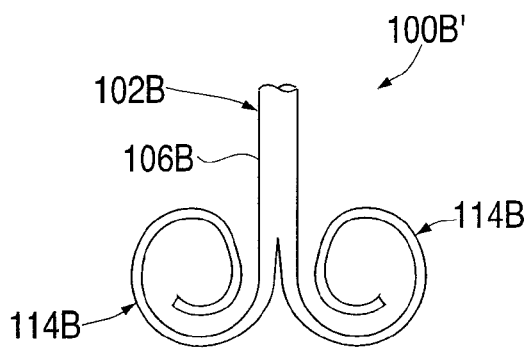
FIG. 7A is a side view of a portion of a ureteral stent according to an embodiment of the invention.
Figure 7B:
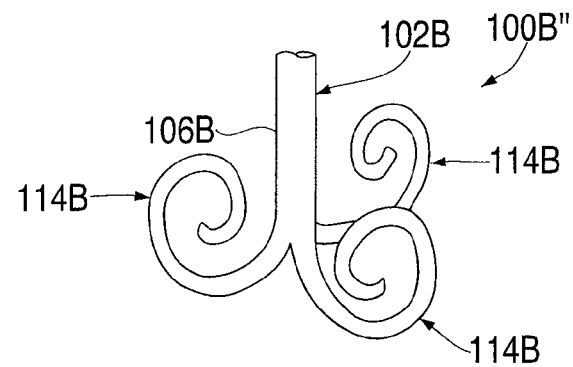
FIG. 7B is a side view of a portion of a ureteral stent according to an embodiment of the invention.
Figure 7C:
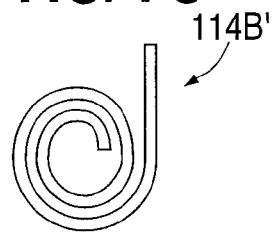
FIGS. 7C-7G are side views of extension members according to several embodiments of the invention.
Figure 7D:
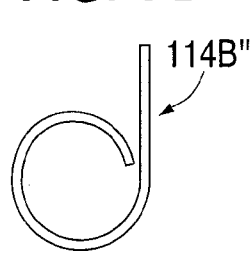
Figure 7E:
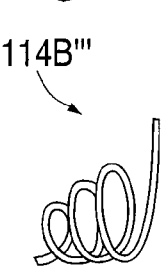
Figure 7F:
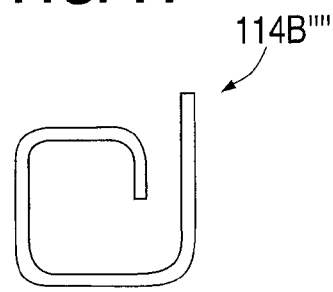
Figure 7G:
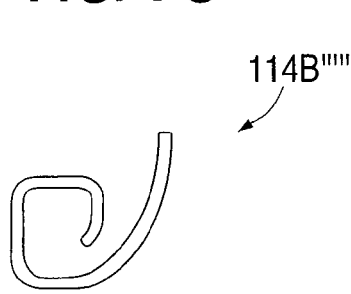

The ureteral stent 100B may include any number of extension members 114B extending from the proximal end portion 106B of the elongate member 102B. For example, FIG. 7A illustrates a portion of a ureteral stent 100B' having two extension members 114B extending from the proximal end portion 106B of the elongate member 102B. FIG. 7B illustrates a portion of a ureteral stent 100B" having three extension members 114B extending from the proximal end portion 106B of the elongate member 102B. In addition, the coil configuration of the extension members 114B may be configured in several different shapes and sizes. Specifically, other embodiments of extension members 114B'-114B"" are illustrated in FIGS. 7C-7G, respectively. Extension members 114B'-114B"" all include a coil configuration having at least one complete turn.

Figure 8A:
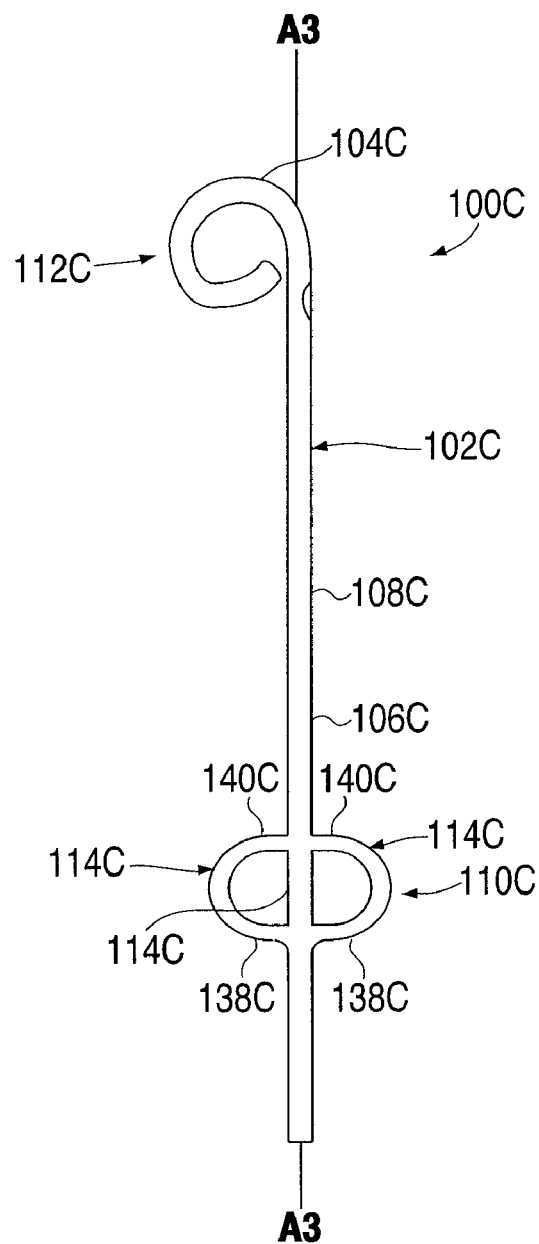
FIG. 8A is a side view of a ureteral stent according to another embodiment of the invention.

FIG. 8A illustrates a ureteral stent according to yet another embodiment of the invention. The ureteral stent 100C is configured substantially similar to and performs substantially the same functions as the previous embodiments. The ureteral stent 100C includes an elongate member 102C having a distal end portion 104C, a medial portion 108C and a proximal end portion 106C. The ureteral stent 100C includes a retention portion 112C configured to be placed in a kidney of a patient and a retention portion 110C configured to be placed in a bladder of the patient. The elongate member 102C defines an axis A3, a lumen (not shown in FIG. 8A), and an opening on the proximal end portion 106C of the elongate member 102C (not shown in FIG. 8A) that communicates with the lumen. In one embodiment, the lumen extends through the retention portion 110C.

The retention portion 110C of ureteral stent 100C includes four extension members 114C extending from the proximal end portion 106C of the elongate member 102C. The extension members 114C extend in a direction away from the axis A3 defined by the elongate member 102C and include a proximal end 138C and a distal end 140C. The proximal end 138C of each of the extension members 114C are coupled together, as shown in FIG. 8A.

Figure 8B:
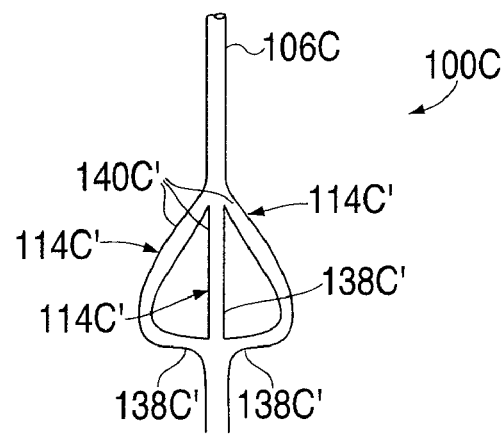
FIG. 8B-8E are side views of a portion of a ureteral stent according to several embodiments of the invention.
Figure 8C:
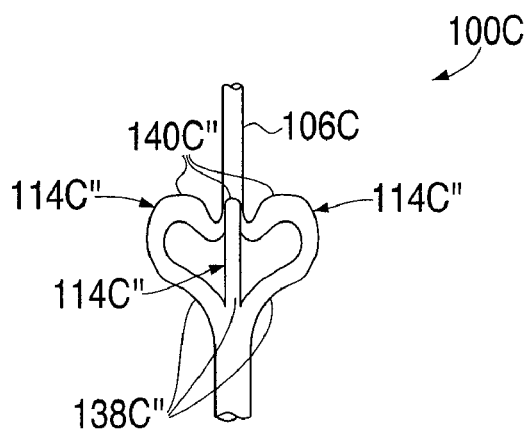
Figure 8D:
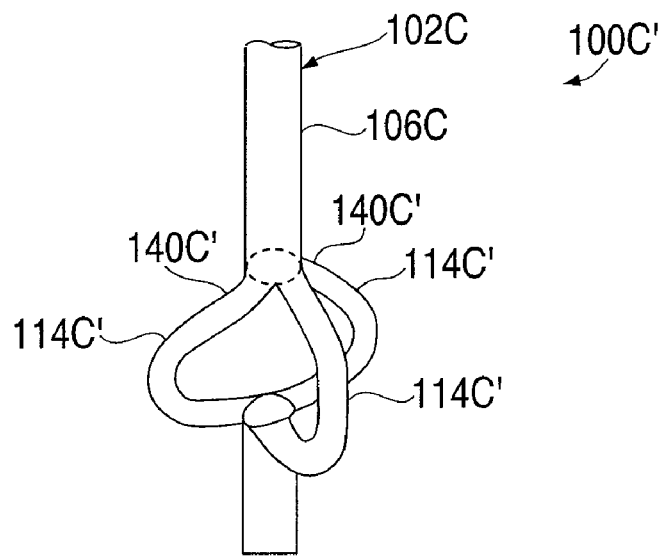
Figure 8E:
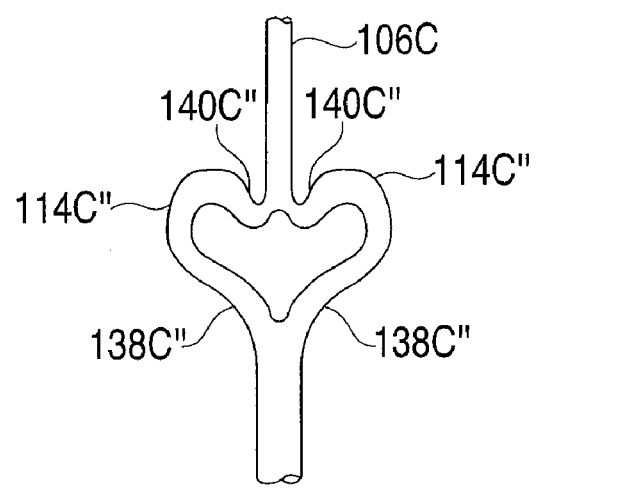

As with the previous embodiments, the ureteral stent 100C may include any number of extension members 114C extending from the proximal end portion 106C of elongate member 102C. For example, FIGS. 8A, 8B, and 8C all illustrate embodiments of ureteral stent 100C having four extension members. FIG. 8D illustrates an embodiment of ureteral stent 100C' having three extension members. FIGS. 8E and 9B illustrate embodiments of ureteral stent 100C'' having two extension members. In addition, the extension members may be formed in a variety of different shapes and sizes. For example, FIG. 8A illustrates an embodiment of ureteral stent 100C having extension members 114C. FIGS. 8B and 8D illustrate embodiments of a ureteral stent having extension members 114C'. FIGS. 8C and 8E illustrate further embodiments of a ureteral stent having extension members 114C''. FIG. 9B illustrates a ureteral stent having extension members 114C'''. The extension members 114C-114C''' may be formed monolithically with the elongate member as described above for the previous embodiments. Specifically, in one embodiment, the elongate member is split to form the extension members. As shown, for example, in FIGS. 8A-8E and 9B, the extension members 114C-114C''' can define multiple openings in a wall of the elongate member, and the openings can be disposed at a distance from a proximal end of the elongate member. In addition, in one embodiment, the extension members 114C-114C''' are homogenously constructed and have a solid cross-section as shown for extension members 114C''' in FIG. 9C. The solid cross-section extends from the proximal end to the distal end of each of the extension members 114C-114C'''.

Figure 9A:
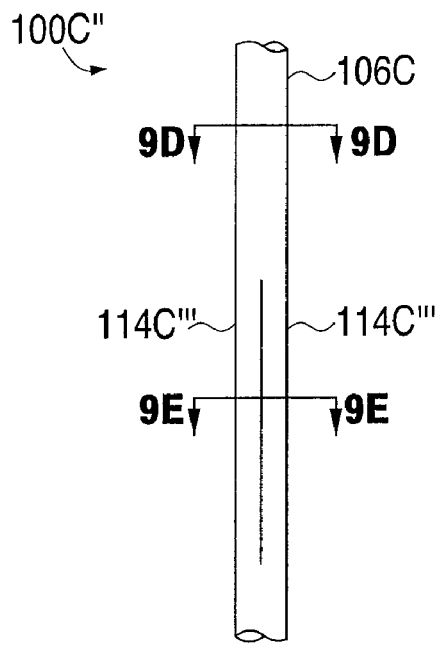
FIG. 9A is a side view of a portion of a ureteral stent according to an embodiment of the invention shown in a constrained configuration.
Figure 9B:
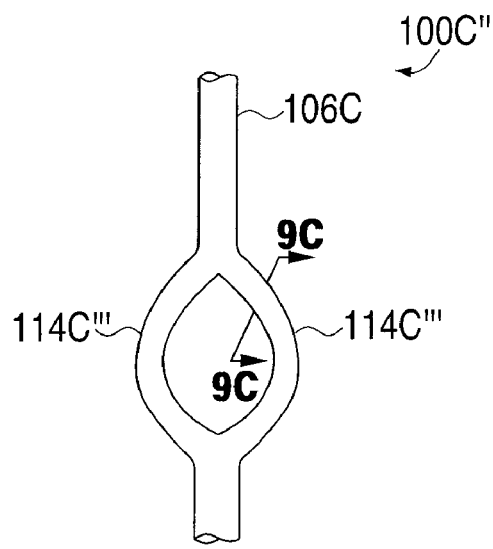
FIG. 9B is a side view of a portion of the ureteral stent of FIG. 9A shown in an unconstrained configuration.
Figure 9D:
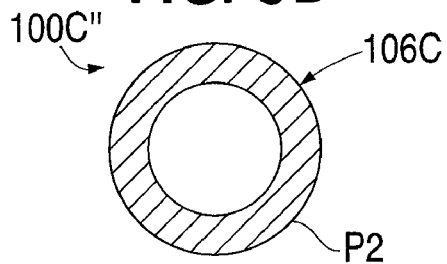
FIGS. 9D and 9E are cross-sectional views taken along lines 9D-9D and 9E-9E, respectively, in FIG. 9A.
Figure 9C:
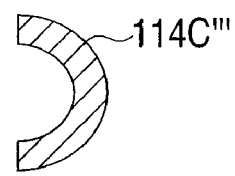
FIG. 9C is a cross-sectional view taken along line 9C-9C in FIG. 9B.
Figure 9E:
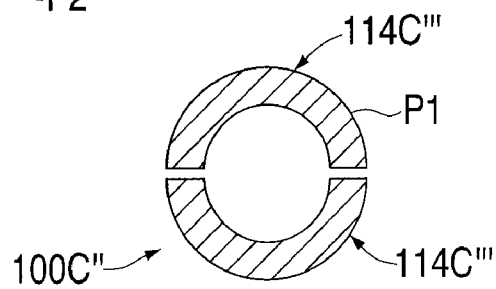

The extension members 114C''' (114C-114C'') are configurable between a constrained configuration, as shown in FIG. 9A, and an unconstrained configuration, as shown in FIGS. 8A-8E and 9B. In the constrained configuration, the proximal end portion 106C of the elongate member 102C defines a perimeter P2 as shown in FIG. 9D, and the extension members 114C''' collectively define a perimeter P1 as shown in FIG. 9E. The perimeter P2 defined by the elongate member 102C is substantially the same size as the perimeter P1 defined collectively by the extension members 114C'''. In some embodiments, in the constrained configuration the extension members 114C''' are capable of being contained within the perimeter P2 of the elongate member 102A.

In addition, in the unconstrained configuration the extension members 114C''' (114C-114C'') are spaced apart from each other and are flexible yet sufficiently rigid to collectively help retain at least a portion of the ureteral stent 100C (100C', 100C'') within the bladder of the patient.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

For example, a ureteral stent according to the invention may include one or more extension members extending from the elongate member. The extension members may be configured in a variety of different shapes and sizes and in some embodiments include an end portion. In some embodiments, the extension members are homogenous and have a solid cross-section. In some embodiments, the extension members are formed monolithically with the elongate member. In other embodiments, the extension members are coupled to the elongate member.

In some embodiments, the elongate member defines a lumen extending from the distal end portion to the proximal end portion. In other embodiments, the elongate member does not define a lumen. In addition, in some embodiments, the extension members extend away from the axis defined by the elongate member, in some embodiments the extension members extend away from the opening defined by the elongate member and in some embodiments, the extension members extend away from both the axis and the opening defined by the elongate member.

What is claimed is:

1. A ureteral stent, comprising:
an elongate member having a proximal end portion and a distal end portion and defining a longitudinal axis;
a first extension member extending from the proximal end portion of the elongate member, the first extension member including a first portion, a second portion, and a third portion including an end portion and having an unconstrained configuration in which the first portion is arcuate and extends in a direction away from the longitudinal axis of the elongate member, the second portion extends from the first portion in a distal direction, and the third portion extends from the second portion in a direction away from the longitudinal axis of the elongate member such that the end portion is disposed at a lateral distance from the elongate member measured in a direction substantially perpendicular to the longitudinal axis of the elongate member that is greater than a lateral distance from the elongate member of the first portion measured in a direction substantially perpendicular to the longitudinal axis of the elongate member and a lateral distance from the elongate member of the second portion measured in a direction substantially perpendicular to the longitudinal axis of the elongate member; and
a second extension member extending from the proximal end portion of the elongate member, the second extension member including a first portion, a second portion, and a third portion including an end portion and having an unconstrained configuration in which the first portion is arcuate and extends in a direction away from the longitudinal axis of the elongate member, the second portion extends from the first portion in a distal direction, and the third portion extends from the second portion in a direction away from the longitudinal axis of the elongate member such that the end portion is disposed at a lateral distance from the elongate member measured in a direction substantially perpendicular to the longitudinal axis of the elongate member that is greater than a lateral distance from the elongate member of the first portion measured in a direction substantially perpendicular to the longitudinal axis of the elongate member and a lateral distance from the elongate member of the second portion measured in a direction substantially perpendicular to the longitudinal axis of the elongate member, when in the unconstrained configurations, the first extension member and the second extension member collectively configured to retain the elongate member within a urinary track of a patient.

2. The ureteral stent of claim 1, wherein the distal end portion of the elongate member is configured to be placed in a kidney of the patient.

3. The ureteral stent of claim 1, wherein in the unconstrained configurations the first extension member is configured to contact a bladder wall of the patient at a first contact location, the second extension member is configured to contact the bladder wall of the patient at a second contact location, the first contact location and the second contact location are disposed at a spaced distance from a ureter entrance of the patient.

4. The ureteral stent of claim 1, wherein the elongate member defines a lumen that extends between the proximal end portion and the distal end portion of the elongate member.

5. The ureteral stent of claim 1, wherein the first extension member and the second extension member are formed monolithically with the elongate member.

6. The ureteral stent of claim 1, wherein the first extension member and the second extension member are each configurable in a constrained configuration by urging the end portion of the first extension member and the end portion of the second extension member toward each other and in a proximal direction until the end portion of the first extension member and the end portion of the second extension member are substantially adjacent each other.

7. The ureteral stent of claim 1, wherein the elongate member defines a lumen that extends between the proximal end portion and the distal end portion of the elongate member, the elongate member defining an opening on the proximal end portion in fluid communication with the lumen, the first portion of the first extension member extends in a direction away from the opening when the first extension member is in its unconstrained configuration, the first portion of the second extension member extends in a direction away from the opening when the second extension member is in its unconstrained configuration.

8. The ureteral stent of claim 1, wherein the elongate member defines a perimeter, the first extension member and the second extension member are each configurable in a constrained configuration in which the perimeter defined by elongate body is substantially the same size as a perimeter defined collectively by the first extension member and the second extension member in the constrained configurations.

9. The ureteral stent of claim 1, wherein the elongate member defines a perimeter, the first extension member and the second extension member are each configurable in a constrained configuration in which the first extension member and the second extension member define a perimeter contained within the perimeter of the elongate member.

10. A ureteral stent, comprising:

an elongate member defining a perimeter and having a proximal end and a distal end, the elongate member defining a longitudinal axis;

a first extension member extending from the proximal end of the elongate member, the first extension member having a first portion, a second portion and an end portion, and having an unconstrained configuration in which the first portion extends from the proximal end of the elongate member in a direction away from the perimeter defined by the elongate member and curves in a first direction about a first axis disposed at a first lateral distance from the longitudinal axis of the elongate member measured in a direction substantially perpendicular to the longitudinal axis of the elongate member, the second portion extends from the first portion and curves in a second direction opposite the first direction about a second axis disposed at a second lateral distance from the longitudinal axis of the elongate member measured in a direction substantially perpendicular to the longitudinal axis of the elongate member and distal of the first axis, and the end portion extends from the second portion and is disposed distally of the proximal end of the elongate member; and a second extension member extending from the proximal end of the elongate member, the second extension member having a first portion, a second portion and an end portion, and having an unconstrained configuration in which the first portion extends from the proximal end of the elongate member in a direction about a first axis disposed at a first lateral distance from the longitudinal axis of the elongate member measured in a direction substantially perpendicular to the longitudinal axis of the elongate member, the second portion extends from the first portion and curves in a second direction opposite the first direction about a second axis disposed at a second lateral distance from the longitudinal axis of the elongate member measured in a direction substantially perpendicular to the longitudinal axis of the elongate member and distal of the first axis, and the end portion extends from the second portion and is disposed distally of the proximal end of the elongate member, when in the unconstrained configurations, the first extension member and the second extension member collectively configured to retain the elongate member within a urinary track of a patient.

11. The ureteral stent of claim 10, wherein the distal end of the elongate member is configured to be placed in a kidney of the patient.

12. The ureteral stent of claim 10, wherein in the unconstrained configurations at least a portion of the first extension member is configured to contact a bladder wall of the patient at a first contact location, at least a portion of the second extension member is configured to contact the bladder wall of the patient at a second contact location, the first contact location and the second contact location being disposed at a non-zero distance from a ureter entrance of the patient.

13. The ureteral stent of claim 10, wherein the elongate member defines a lumen between the proximal end and the distal end of the elongate member.

14. The ureteral stent of claim 10, wherein the first extension member and the second extension member are each formed monolithically with the elongate member.

15. The ureteral stent of claim 10, wherein the elongate member defines a lumen that extends between the proximal end and the distal end of the elongate member, the elongate member defines an opening on the proximal end in fluid communication with the lumen, a first portion of the first extension member and a first portion of the second extension member each extend from the proximal end of the elongate member in a direction away from the opening when the first extension member and the second extension member are each in their unconstrained configurations.

16. The ureteral stent of claim 10, wherein the first extension member and the second extension member are biased into their unconstrained configurations and are'collectively configurable in a constrained configuration in which the perimeter defined by the elongate member is substantially the same size as a perimeter defined collectively by the first extension member and the second extension member in the constrained configuration.

17. A ureteral stent, comprising:

an elongate member defining a longitudinal axis and having a proximal end portion and a distal end portion; and an extension member extending from the proximal end portion of the elongate member and having an unconstrained configuration in which a first portion of the extension member extends from the proximal end portion of the elongate member and curves in a first direction approximately 180 degrees, and a second portion of the extension member extends from the first portion and curves in a direction opposite the first direction and is disposed laterally of the elongate member and distally of a proximal end of the elongate member, when in the unconstrained configuration the extension member configured to maintain the elongate member within a urinary track of a patient.

18. The ureteral stent of claim 17, wherein the extension member is a first extension member, the ureteral stent further comprising:

a second extension member, the second extension member extending from the proximal end portion of the elongate member and having an unconstrained configuration in which a first portion of the second extension member extends from the proximal end portion of the elongate member and curves in a first direction approximately 180 degrees, and a second portion of the second extension member extends from the first portion and curves in a direction opposite the first direction and is disposed laterally of the elongate member and distally of a proximal end of the elongate member.

19. The ureteral stent of claim 17, wherein the extension member is a first extension member, the ureteral stent further comprising:

a second extension member, the second extension member extending from the proximal end portion of the elongate member and having an unconstrained configuration in which a first portion of the second extension member extends from the proximal end portion of the elongate member and curves in a first direction approximately 180 degrees, and a second portion of the second extension member extends from the first portion and curves in a direction opposite the first direction and is disposed laterally of the elongate member, when in their unconstrained configurations, the first extension member and the second extension member being disposed on opposite sides of the elongate member in a side view.

20. The ureteral stent of claim 17, wherein the extension member is formed monolithically with the elongate member.

21. The ureteral stent of claim 1, wherein when in the unconstrained configurations, the first portion, second portion and third portion of the first extension member and the first portion, second portion and the third portion of the second extension member are collectively configured to retain the elongate member within a urinary track of a patient.

* * * * *